United States Patent [19]
Torres-Ibanez

[11] Patent Number: 5,050,426
[45] Date of Patent: Sep. 24, 1991

[54] METHOD FOR DETERMINING THE RELIABILITY OF MEN'S CONTRACEPTIVES

[76] Inventor: Jos'e Torres-Ibanez, Tuset 19, Barcelona, Spain

[21] Appl. No.: 454,045
[22] Filed: Dec. 20, 1989
[51] Int. Cl.$^5$ ............................................. G01M 3/04
[52] U.S. Cl. .......................................... 73/45.5; 73/12
[58] Field of Search .................... 73/45.5, 37, 12, 807, 73/840

[56] References Cited
FOREIGN PATENT DOCUMENTS
553390 4/1977 U.S.S.R. .................................. 73/37
1283600 1/1987 U.S.S.R. .................................. 73/37

OTHER PUBLICATIONS
Kinderhauser, V. et al. An Electronically Controlled... Pressure. Biomed. Techn. (German) vol. 24; No. 9, Sep. '79; pp. 198-203.

Primary Examiner—Jerry W. Myracle
Attorney, Agent, or Firm—McGlew & Tuttle

[57] ABSTRACT

Method for determining the reliability of men's contraceptives, characterized by submerging the contraceptive in a liquid, injecting a liquid in impulses into the contraceptive, and generating shock waves.

3 Claims, 1 Drawing Sheet

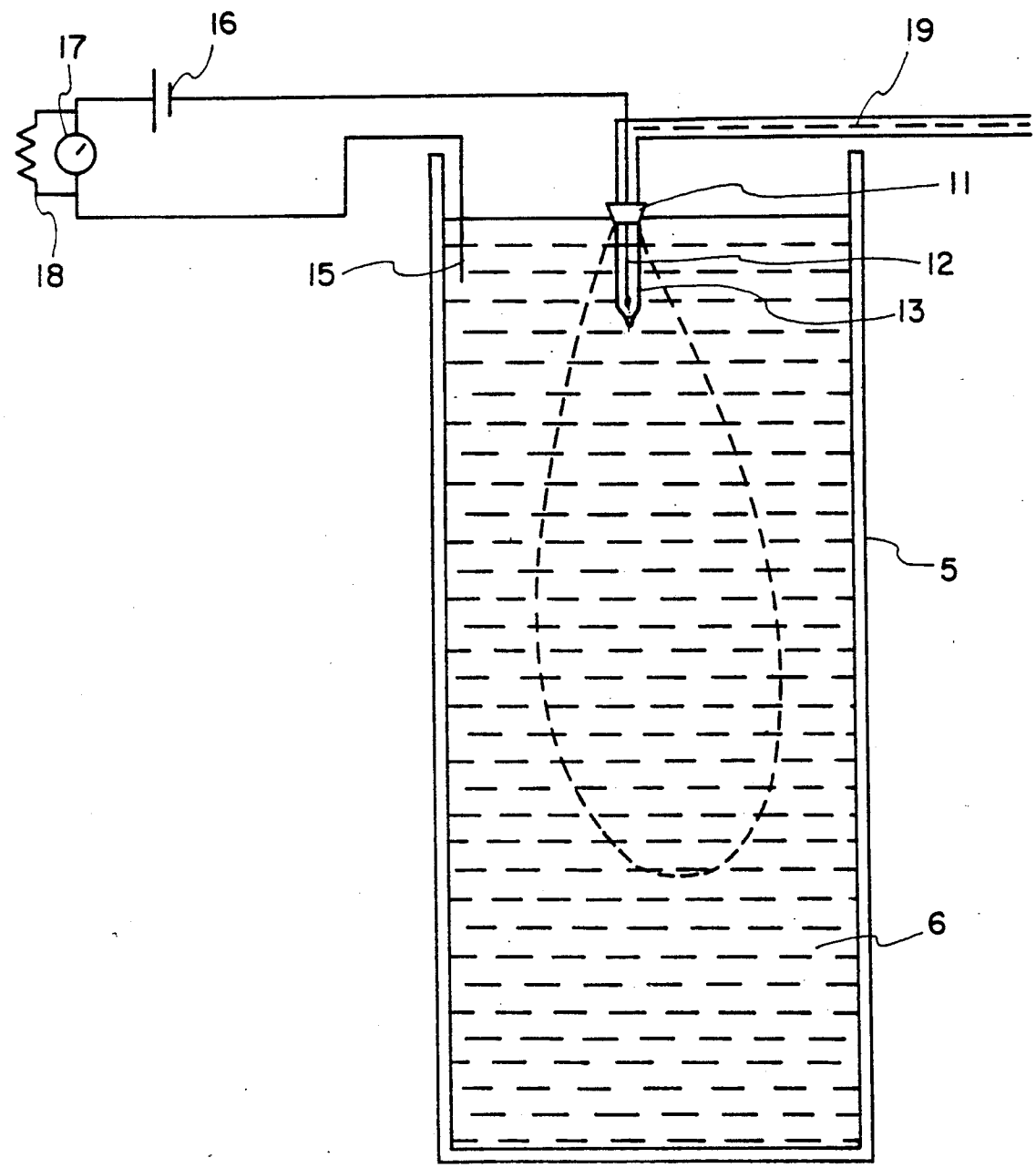

METHOD FOR DETERMINING THE RELIABILITY OF MEN'S CONTRACEPTIVES

The present invention pertains to a method for determining the reliability of men's contraceptives.

Elastomers such as rubber and latex, etc., usually vulcanized or polymerized, possess elastic properties, are subject to deformation, and can fit tightly around the bodies to which they are applied because of their reduced thickness. For this reason, such elastomers are used in the manufacture of contraceptives or condoms, in the form of a thin sheath, flexible and impermeable, placed over the erect penis to keep the semen from penetrating into the vagina during sexual intercourse. Condoms are also used to prevent the sexual transmission of some diseases and to collect semen for clinical purposes (analysis, etc.).

Conventionally, condoms may offer a receptacle for semen at their closed extremity and normally have a reinforced edge on their open side. They may be transparent, translucent, opaque or colored, dry or lubricated, with a smooth or wrinkled surface.

Condoms must also be free from impurities, especially substances harmful to health.

Because of their particular nature (composition and structure of molecular arrangement) elastomers can be easily molded, generally by immersion (more than once if necessary) of corresponding molds into a natural latex bath including stabilizers, antioxidants, crosslinking agents, accelerators, etc. Condoms formed from the elastomers are dried (e.g., with hot air) after molding and undergo a final polymerization (accelerated by heat in this case) and a subsequent washing and packing, with the addition of lubricants if needed. Such a process results in lots of contraceptives with little homogeneity. The standard processes result in a great disparity as to, among other things, physical characteristics, including pores and/or cuts that affect impermeability of the condoms and, hence, their degree of reliability (these pores and cuts may occur because of the presence of bubbles in the latex baths or because of unwanted contractions during drying or polymerization).

To determine the contraceptives' reliability, various quality control tests have been proposed and utilized, including destructive tests, which originate from other fields of industry, such as textiles, paper-making and motor vehicle tires.

These tests include, e.g., the tensile strength test and the test to determine minimum stretching upon rupture, performed by cutting a fragment or specimen of the contraceptive to be assayed, which is pulled to the breaking point, and measuring the tensile strength and the elongation during this rupture. Another test is the the test of volume and explosion pressure in which a constant length of the contraceptive is inflated with air and the volume and pressure noted at the time of explosion, the inflating being done with clean air at an average, constant and determined volume. Still another test is the color stability test, in the case of pigmented contraceptives, in which the product to be tested is soaked in distilled water and wrapped in white absorbent paper. After a certain length of time, the paper is examined for possible traces of dye. A stability test is also used during storage of the contraceptives, by accelerated aging, since elastomers tend to deteriorate with time, for mechanical reasons, due to the action of light, etc. The corresponding contraceptives to be examined will be submitted to the above-described tensile strength tests; the elongation is observed at the moment of rupture; the tensile properties and/or the pressure and explosion volume are measured after the contraceptives have been kept in their packages at a high temperature over a set period of time; and the test for the detection of holes in porous zones, which can be performed by filling the contraceptive with a determined amount of water and examining it in order to detect any water leak through its side. Or else, it can be realized on the basis of a conductivity method, by means of a metal container serving as an electrode and full of salt water, into which one introduces the contraceptive to be tested; the latter is also filled with a saline solution and one places into it another electrode connected to a source of direct current, a resistor and a voltmeter enabling the detection of any leak that would be indicated by current passing through the electrical circuit.

The tests mentioned are destructive in themselves, or the contraceptive must always be destroyed once it has been tested.

Also well-known is a destructive test in which a constant volume of water is injected to the interior of the contraceptive until it breaks in air.

In the already known tests that were mentioned, with injection of water or air inside the contraceptive placed in air, the introduction of fluid occurs at a constant volume, so that, in these tests, conventional contraceptives always composed of macromolecules (such as polyisoprene in latex) are subjected to increasing stresses which grow at a constant rate. Consequently, these tests do not make it possible to detect the metastable equilibria in which their molecules find or may find themselves. On the other hand, during normal use, the contraceptives are exposed to stresses whose rate of variation is not constant, and such stresses are not homogeneous. As a result, even though the theoretical risk of rupture for contraceptives is admitted around 0.6%, in practice it is in the order of 1 to 8% and even higher.

SUMMARY AND OBJECT OF THE INVENTION

As a science, rheology studies the deformation and fluidity of substances, in particular non-Newtonian and plastic fluidity. This science especially applies to elastomers from which contraceptives are manufactured. As theories developed in rheology, one may cite those corresponding to the ideal elastic body or Hookean solid, to the viscous body, according to Newton's law, with the Lennard-Jones equation, to the viscoelastic body studied by Arridge, considering distortions and changes of shape as phase shifts in which the distances between molecules are maintained, and whose study give rise to curves showing metastable zones of moments of equilibrium. One must also mention the following classification of rheological measurements according to viscoelastic models: static ones in which the stress or deformation remains constant during the measuring of the test; transitory ones in which the stress or deformation applied increases constantly over time, i.e., at a constant rate; and dynamic ones in which the stress or deformation is applied according to a time function of the sinusoidal or sawtooth type, and the variable is measured at its value and in its phase shift in respect to time.

Also proposed were viscoelastic models such as the Maxwell body, which is studied as a Hookean solid, then as a Newtonian body. As a result, the polyisoprene latex, in a first approximation, behaves like a Maxwell body as the original stresses applied to it produced an elastic (linear) response. If the load is kept up, the viscous component intervenes and, when the load is withdrawn, the body goes back to being elastic, but with a permanent deformation. Another theory, said to be related to Smith fractures, illustrates the effect of time factor influence through a series of fractures in a stress-strain diagram at different traction velocities. In this case, it is explained that the fragile rupture zone corresponds to a rupture in which there was no time for relaxation or internal flow of the material because of the relatively high test velocities.

The main rheological criteria of interest to the present invention is the rupture of materials based on the rupture originating from: a molecular separation, when the Lennard-Jones potential is surpassed, the rupture occurring by physical separation between two molecules, as the intermolecular or Van-der-Waals forces that unite them are overcome; the exceeding of the viscoelastic limit as per the studies performed by Kaelbe; and from imperfections (cracks and holes) in the macromolecules, according to the crack propagation theory studied by Griffith, with a comparison of the rate of propagation to the stresses of the test.

It has been confirmed experimentally that, to overcome the drawbacks particular to the known tests, while bearing in mind the various rheological theories, dynamic tests are essential for the elimination of metastable equilibria, liable to be considered as true molecular obstructions, which stop being stable because of a molecular vibration or because of time. Aside from this, there have been experiments with an analogous model as close as possible to the actual utilization of the contraceptives.

To this effect, the present invention proposes a new industrial method for determining the reliability of condoms. This method is characterized by submerging the contraceptive in a liquid held in a suitable container, injecting into the contraceptive a liquid with impulses, and generating shock waves capable of rupturing the contraceptive with low reliability. As an option, there is an interesting realization of this method featuring the additional introduction into the contraceptive of an electrode connected to a source of electricity; this source is in turn connected to a parallel group consisting of a suitable voltmeter and a resistor, the group being finally connected to another electrode introduced into the container's liquid. The purpose is to detect the existence of holes and/or porous zones in the contraceptive and cause it to break.

Through the application of the method according to the present invention, the contraceptives are treated as bodies that are not crystalline, as in reality, in a dynamic industrial test, which detects and eliminates contraceptives not suitable for use. The shock waves cause the unreliable contraceptive to break as its film is unstable due to metastable equilibria in the material. Such defective condoms would not rupture during the tests of the prior art and their defects would not show up in such tests; accordingly, they would be regarded as acceptable products.

In comparison with the already existing tests and methods, the application of the method according to the present invention provides the advantages described, in addition to other advantages, which will be easily inferred by a person skilled in the art. Below is a description of an example of the realization of this method, to make it easier to understand the previously explained characteristics. At the same time, various details of its execution are described.

BRIEF DESCRIPTION OF THE DRAWING

The sole FIGURE of the accompanying drawing is a schematic view illustrating the application of a preferred example of the method of the invention.

DETAILED DESCRIPTION OF THE INvENTION

According to a prefered form of the invention a container 5 made of insulating material such as plastic is prepared and filled with water 6, a certain amount of salt is dissolved in the water 6 to promote conductivity. The contraceptive 13 to be tested is placed on a suitable stand 11, positioned hanging vertically downward. The stand 11 is fixed over the container 5, so that the contraceptive 13 is conveniently submerged in the liquid inside the container 5. An electrode 15 is introduced into the liquid. Through the stand, another electrode 12 is inserted into the hanging contraceptive's cavity. This last electrode 12 is connected to a source 16 of low-voltage electricity, for instance, 10 V a.c. (direct current could be used, but it is less effective). The power source 16 is, in turn, connected to an integrated group containing a voltmeter 17 and a resistor 18 connected in parallel. The group itself is connected to the electrode 15 directly submerged in the liquid held in the container 5.

After this installation is completed, a liquid 10, such as water, is injected into the contraceptive 13. Characteristically, this injection takes place according to a pulsating mode or with impulses, preferably but not exclusively of the sawtooth type. This creates shock waves, which cause the rupture of a defective or unreliable contraceptive 13. At the same time, possible holes or pores in the contraceptive 13 are detected through the voltage that may be indicated by the voltmeter 17, signaling the passage of some current between the two electrodes 12 and 15, or through the resistor 18 connected in parallel to the voltmeter 17, which represents a passage of current through the contraceptive's wall and, consequently, one hole or more and/or one pore or more in the contraceptive 13. Such an indication of course entails that the contraceptive 13 is unusable and, as a result, the lot to which it belonged is to be rejected and should be destroyed.

If a metal container is used, its own body may serve as the submerged electrode 15 inside the container's liquid, which it replaces.

It should be noted that the application of the above-described method represents the rupture of only the unreliable or defective contraceptives, even in the case in which no holes, cavities or pores have been detected in the treated condom. Consequently, one should reject the lots or shipments in which the representative contraceptive or the contraceptives used as specimens have ruptured during the treatment according to the method described here.

In cases in which the contraceptives are used in bulk or in large quantities, the method is applied to statistically designated samples of each lot or shipment, aside from the other tests that were previously described. Through this method, the rejected and approved specimens are determined, the latter serving as patterns for the mass production of contraceptives. Once accepted, the contraceptives are again treated according to the method of the present invention. The conventional tests that are deemed of interest are also repeated. The manufacturing process ends with the rolling-up of the contraceptives and their lubrication, e.g., with silicone oils, hermetic unit packaging and packing in boxes.

Before shipping a large quantity of contraceptives, a treatment according to the method described here is again applied, aside from the other mandatory conventional tests (such as the stability test during storage under accelerated aging conditions as was explained above).

It must be pointed out that in realizing the object of the present patent, it is possible to apply all the variations of detail which may be advised by experience or practice, especially in regard to complementary phases or operations and other circumstances of detail that are compatible with the essential nature of the method as set forth in the claims.

While a specific embodiment of the invention has been shown and described in detail to illustrate the application of the principles of the invention, it will be understood that the invention may be embodied otherwise without departing from such principles.

What is claimed is:

1. A method for determining the reliability of condoms, comprising the steps of:

submerging the condom in a first liquid disposed in a container, injecting a second liquid into the condom in pulses to generate shock waves capable of rupturing a condom of low reliability.

2. A method of determining the reliability of a condom according to claim one, further comprising the steps of positioning an electrode within the condom, the electrode being connected to a source of electricity, which is in turn connected to a parallel group consisting of a volt meter and a resistor; connecting said parallel group to another electrode and connecting said another electrode into electrical contact with said liquid in said container and detecting electrical current flow as an indication of the existence of holes and/or porous zones in the condom.

3. A method of determining the reliability of a condom, comprising steps of: inserting a condom into a liquid provided in a container such that a first side of said condom is in contact with said liquid and injecting a liquid into the other side of said condom in pulses for generating shock waves capable of rupturing a condom of low reliability.

* * * * *